(12) United States Patent
Drenguis (10) Patent No.: US 8,884,249 B2
(45) Date of Patent: Nov. 11, 2014

(54) DEVICE FOR STERILIZING CLOSURES FOR CONTAINERS

(75) Inventor: Alfred Drenguis, Bornsen (DE)

(73) Assignee: KHS GmbH, Dortmund (DE)

( * ) Notice: Subject to any disclaimer, the term of this patent is extended or adjusted under 35 U.S.C. 154(b) by 27 days.

(21) Appl. No.: 13/879,141

(22) PCT Filed: Sep. 13, 2011

(86) PCT No.: PCT/EP2011/004595
§ 371 (c)(1),
(2), (4) Date: Apr. 12, 2013

(87) PCT Pub. No.: WO2012/069101
PCT Pub. Date: May 31, 2012

(65) Prior Publication Data
US 2013/0193344 A1    Aug. 1, 2013

(30) Foreign Application Priority Data

Nov. 24, 2010  (DE) .......................... 10 2010 052 207

(51) Int. Cl.
*H01J 37/20* (2006.01)
*B67B 3/00* (2006.01)
*A61L 2/10* (2006.01)

(52) U.S. Cl.
CPC . *A61L 2/10* (2013.01); *B67B 3/003* (2013.01); *A61L 2202/23* (2013.01)
USPC ............. 250/455.11; 250/453.11; 250/454.11

(58) Field of Classification Search
None
See application file for complete search history.

(56) References Cited

U.S. PATENT DOCUMENTS

| | | | | |
|---|---|---|---|---|
| 2,175,682 A * | 10/1939 | Chaffee | ............................ | 141/85 |
| 4,342,346 A * | 8/1982 | Wei | ..................... | 141/85 |
| 4,877,964 A * | 10/1989 | Tanaka et al. | ............. | 250/455.11 |
| 4,880,120 A * | 11/1989 | Myers et al. | .................... | 209/3.1 |
| 4,981,649 A * | 1/1991 | Shibauchi et al. | ............... | 422/24 |
| 5,958,336 A * | 9/1999 | Duarte | ............................ | 422/24 |
| 6,066,081 A * | 5/2000 | Bachner | ........................ | 493/102 |
| 6,710,357 B1 * | 3/2004 | Schweitzer | ................ | 250/492.1 |
| 7,703,262 B2 * | 4/2010 | Till | ................. | 53/426 |
| 2003/0046897 A1 * | 3/2003 | Kitajima et al. | .............. | 53/133.2 |
| 2007/0157559 A1 * | 7/2007 | Till | ................. | 53/411 |
| 2009/0252646 A1 * | 10/2009 | Holden et al. | ................... | 422/24 |
| 2011/0155915 A1 * | 6/2011 | Brueck et al. | ............... | 250/354.1 |
| 2012/0180439 A1 * | 7/2012 | Klenk | .............................. | 53/558 |

FOREIGN PATENT DOCUMENTS

| | | |
|---|---|---|
| EP | 1120121 | 8/2001 |
| EP | 1982921 A1 * | 10/2008 |
| EP | 1982921 B1 * | 8/2012 |
| GB | 1093751 | 12/1967 |

(Continued)

*Primary Examiner* — Andrew Smyth
(74) *Attorney, Agent, or Firm* — Occhiuti & Rohlicek LLP (57) ABSTRACT

An apparatus for sterilizing cap-like closures for closing bottles includes a conveying system to move the cap-like closures through a treatment zone in which the cap-like closures are exposed to ultraviolet radiation for sterilization, the treatment zone having ultraviolet radiation sources for emitting ultraviolet light. Within the treatment zone, the conveying system includes a rotor that can be driven to rotate about a vertical rotor axis, and closure holders formed on a periphery of the rotor. Each closure holder is oriented with a longitudinal extension thereof in a direction of the rotor axis. The closure holders are configured for moving the cap-like closures vertically from top to bottom through the treatment zone on a treatment section between a closure supply and a closure discharge.

12 Claims, 8 Drawing Sheets

(56) References Cited

FOREIGN PATENT DOCUMENTS

| | | | | |
|---|---|---|---|---|
| JP | 63281936 A | * | 11/1988 | ............ B65B 55/08 |
| JP | 4242525 | | 8/1992 | |
| JP | 2001171621 A | * | 6/2001 | ............ B65B 55/08 |
| JP | 4242525 B2 | * | 3/2009 | |
| WO | 2006106363 | | 10/2006 | |
| WO | WO 2006106363 A2 | * | 10/2006 | |
| WO | WO 2006106363 A3 | * | 6/2007 | |

* cited by examiner

DEVICE FOR STERILIZING CLOSURES FOR CONTAINERS

CROSS REFERENCE TO RELATED APPLICATION

This application is the national phase under 35 USC 371 of international application no. PCT/EP2011/004595, filed Sep. 13, 2011, which claims the benefit of the priority date of German application no. 10 2010 052 207.4, filed Nov. 24, 2010. The contents of the aforementioned applications are incorporated herein in their entirety.

FIELD OF DISCLOSURE

The invention relates to a device for disinfecting or sterilising closures.

BACKGROUND

For example in plants in the drinks industry, it is common and known to sterilise or disinfect the closures used to close filled bottles or other containers, in particular cap-like closures such as screw closures, flat caps, crown corks etc., before use i.e. before their application to the respective container.

For this sterilisation, amongst others UV radiation, in particular UV-C radiation, is suitable, to which the closures are exposed on their outer and inner face for a sufficient treatment duration, for example for a treatment time of around 120 seconds.

UV radiation sources in the sense of the invention are in particular all known UV radiation sources or UV lamps, amongst others mercury-doped high-pressure and low-pressure lamps or high-pressure and low-pressure gas discharge lamps, but also quartz lamps, deuterium lamps etc. emitting UV radiation. Preferably the UV radiation sources in the sense of the invention are low-pressure gas discharge lamps emitting UV light and preferably rod-shaped, low-pressure, gas discharge lamps emitting UV light.

The term "substantially" in the sense of the invention means deviations from the precise value by +/−10%, preferably +/−5% and/or deviations in form of changes irrelevant to function.

SUMMARY

The object of the invention is to provide a device which, with a high sterilisation quality or disinfection rate, also allows a reproducible high performance (number of sterilised or disinfected closures per time unit).

Particular advantages of the device according to the invention lie for example in that despite this high performance, this can be made very compact with little construction space or volume, that constant i.e. reproducibly high disinfection rates are achieved in sterilisation, and that the disinfection or sterilisation takes place without the use of chemicals and at low operating costs, which result amongst others from the reduced power consumption above all for the operation of the UV radiation sources and from the long service life of these radiation sources. The device according to the invention is suitable for closures of widely varying types, in particular also for cap-like closures such as screw closures, flat caps, crown corks etc.

Preferably in the device according to the invention, the at least one treatment chamber is subjected to a slight positive pressure of a sterile gaseous and/or vaporous medium, for example sterile air, so that penetration of ambient air and the germs this carries into the treatment chamber or treatment zone is effectively prevented, above all also in the region of the closure inlets and outlets. The ozone generated by the UV radiation in the treatment chamber also has a sterilising or disinfecting effect on the closures and thus supports the sterilising and/or disinfecting effect of the UV radiation.

Refinements, advantages and possible applications of the invention arise from the description below of embodiment examples and the figures. All features described and/or shown in the figures, alone or in any combination, are in principle the object of the invention irrespective of their summary in the claims or back reference. The content of the claims is declared a constituent part of the description.

BRIEF DESCRIPTION OF THE FIGURES

The invention is explained below with reference to one embodiment example shown in the figures. These show.

DETAILED DESCRIPTION

The device described generally with numeral 1 in the figures serves to sterilise or disinfect closures 2, for example closures in the form of caps, screw caps, sport caps, flat caps or crown corks etc. which are used to close containers not shown e.g. in the form of bottles. For this the device 1 preferably forms an apparatus connected before a closing machine to close the containers, from which apparatus the sterilised closures 2 are supplied to the closing machine under sterile or germ-free conditions.

The device comprises amongst others a device housing 3 which, in the embodiment shown, in top view has a polygonal shape, i.e. is formed hexagonal, surrounding a vertical machine or rotor axis MA. The interior 4 of the housing 3—with the exception of the inlets and outlets for the closures 2—is tightly sealed against the environment, namely by a peripheral wall 5 surrounding the machine axis MA, an upper housing wall 6 hexagonal in the present embodiment, and a lower housing wall 7 also hexagonal. In the peripheral wall 5 are provided inspection windows 8 which are preferably designed impermeable to UV light or at least greatly damping the UV light transmission, for example made of a correspondingly equipped transparent plastic or glass, and/or which can be closed by flaps not shown. On the top of the housing 3 or in the region of the housing wall 6 there is provided a housing part 9 protruding over the top of this housing wall, via which part amongst others the interior 4 can be accessed for repair and/or maintenance purposes.

In the interior 4 of the housing 3 is held a rotor 10 which can be driven circulating about the vertical machine axis MA. In the embodiment shown, the rotor 10 is formed as a circular cylindrical, hollow drum surrounding the machine axis MA concentrically with a drum casing with cage-like structure, which is formed by a multiplicity of closure holders 11 each holding a multiplicity of closures 2. The closure holders 11, which are each oriented with their longitudinal extension parallel or substantially parallel to machine axis MA and at their upper end are open for the introduction of closures 2 and at their lower end are open for the discharge of closures 2, as a whole form the cage- or mesh-like structure or the cage-like, inherently stable casing of the rotor 10 and for this are provided distributed on the periphery of the rotor 10 at equal angular and pitch spacings about the machine axis MA. Ring-like holders 12 concentrically surrounding the machine axis MA and offset to each other in the direction of this axis connect the closure holders 11 together into the grid-like structure of the rotor 10. In the region of their lower ends, the closure holders 11 are attached to a circular disc-shaped carrier element 13 arranged coaxial with the machine axis MA, such that the closure holders 11 each protrude over the periphery of the carrier element 13 and the lower open ends of the closure holders 11 are not covered by the carrier element 13, rather they are exposed in the region of the carrier element 13 or below this carrier element.

The closure holders 11 are also formed mesh-like and each consist of several rod- or bar-like closure guide rails 14 spaced apart from each other and oriented parallel to machine axis MA, which between them form a holding chamber to hold a multiplicity of closures 2 such that the closures 2 in each closure holder 11 form a one-track row or group of closures extending in the axial direction parallel to machine axis MA and are largely exposed as far as possible in the respective closure holder 11 i.e. are covered by the closure guide rails 14 only on a small part of their surface. Furthermore the closure holders 11 in the embodiment shown are designed such that the closures 2 in the closure holders 11 have a predefined orientation in relation to machine axis MA such that they are oriented with their closure or cap axis radial to machine axis MA and for example with their open cap side radially towards the outside.

With the carrier element 13, the rotor 10 is mounted in a bearing 15 on the underside of the housing 3 or on the lower housing wall 7 there, rotatable about the machine axis MA, and can be driven by means of a drive 16 (electric motor with gear) circulating in pulses or steps about the machine axis MA corresponding to arrow A.

UV light sources are provided distributed in the interior 4 of the housing 3 i.e. in the treatment chamber of the device 1 and not circulating with the rotor 10, namely in the embodiment example shown in the form of rod-like UV lamps 17 and 18 which are each held suspended from the upper housing wall 6 or lamp holders 19 there and oriented with their axes parallel to machine axis MA. The outer UV lamps 17 in relation to machine axis MA are arranged radially outside the movement track of the closure holders 11 and the inner UV lamps 18 in relation to machine axis MA are arranged radially inside the movement track of closure holders 11 or the cage-like structure formed by the closure holders 11, namely in the embodiment shown offset to gaps such that in relation to machine axis MA, each inner UV lamp 18 lies radially opposite a gap between two outer UV lamps 17. The number of inner UV lamps 18 is for example the same or approximately the same as the number of closure holders 11 on rotor 10. Preferably however the number of outer UV lamps 17 and inner UV lamps 18 in each case is smaller than the number of closure holders 11. By the arrangement of UV lamps 17 and 18, in particular by the offset arrangement of these lamps, it is guaranteed that the closures held in the closure holders 11 are moved through as even a UV radiation field as possible on the UV treatment section formed by the angular region of the rotary movement of the rotor 10 between the closure supply 20 and the closure discharge 22. The dome-like housing part 9 contains amongst others the electrical function elements which are necessary for controlling the UV lamps 17, 18 and with which UV lamps 17, 18 or their lamp holders 19 are connected via electric lines.

The UV lamps 17 and 18, which are preferably formed identical or substantially identical, each extend with their lower free end up to near the level of the top of the disc-like carrier element 13 and are there spaced slightly from the top or the level of the top of the carrier element. In principle it is possible to form the outer UV lamps 17 with a slightly greater length such that these lamps with their lower free end protrude downwards beyond the plane of the carrier element 13 and extend into a channel-like segment 26 which is formed from the lower housing wall 7 in the outer region of the interior 4 and surrounds the machine axis MA in a circular ring-like manner. This arrangement and formation of the outer UV lamps 17 guarantees particularly reliably that also the bottom closures 2 in the closure holders 11, but also the regions coming into contact with these closures 2, in particular also the surface 25, are intensively treated with or exposed to UV light.

In the upper region of the interior 4 or the treatment chamber formed by this, above the movement track of the closure holders 11 is provided a closure supply 20 which is formed by the lower end of an outer closure transport section 21 and to which the closures to be sterilised are supplied via this closure transport section 21. In the closure transport section 21, the closures already have their orientation corresponding to their orientation in the closure holders 11. In the region of the underside of the housing 3, below the movement track of the closure holders 11, a closure discharge 22 is provided which is substantially formed by the inlet or by an upper open end of the closure transport section 23 which extends through the lower housing wall 7 into the interior 4 and is arranged with its open end below the movement track of the closure holders 11 of the rotor 10 and there forms the closure discharge 22. Via the closure transport section 23, the sterilised closures 2 are supplied germ-free to the closing machine not shown. In addition to the closure discharge 22 and the closure transport section 23, a closure discharge formed by a closure guide 24 is provided below the movement track of the closure holders 11, via which discharge rapid emptying of the device 1 or rotor 10 is possible i.e. accelerated removal of closures 2 from the closure holders 11, for example on faults in the device 1, in a plant comprising the device 1, on a format change i.e. on conversion from one closure type to another closure type etc.

The closure guide 24 guided out of the housing 3 ends in the interior 4 below the movement track of the closure holders 11. By corresponding control means not shown, the outlet there formed by the closure guide 24 can be controlled such that closures 2 do not enter the closure guide 24 in normal operation of the device 1 but only on accelerated emptying of the device 1 and/or rotor 10.

In the embodiment shown, the closure transport sections 21 and 23 and the closure guide 24 are each formed by several guide rails holding and guiding the closures 2 between them. Furthermore in the embodiment shown the closure transport sections 21 and 23 and the closure guide 24, at least in the vicinity of the device 1, each have a vertical course so that the closures 2 in the closure transport sections 21 and 23 and in the closure guide 24 are transported or moved solely because of gravity. In order however to prevent re-infection of the sterilised closures 2 on the closure transport section 23, this is contained in a casing or housing not shown which is preferably subjected to positive pressure of a sterile gaseous and/or vaporous medium, for example sterile air under positive pressure.

The closure supply 20 and closure discharge 22 in relation to machine axis MA are arranged at an angle spacing which corresponds to a multiple of the pitch spacing of the closure holders 11 on the rotor 10, i.e. so that whenever a closure holder 11 with its open upper end stands at the closure supply 20 in the stoppage phase of the rotary movement of rotor 10, another closure holder 11 with its lower open end stands at the closure discharge 22. Furthermore the closure discharge 22 in relation to the rotation direction A of rotor 10 is spaced by as large an angular amount as possible, i.e. for example by an angular amount of slightly less than 360°, e.g. by an angular amount of 330° or around 330°, from the closure supply 20 in order to achieve as long a treatment section as possible and hence, even at high performance of the device 1 i.e. a high number of closures 2 sterilised per time unit with this device 1 or a correspondingly high rotation speed of the rotor 10, as long a treatment duration as possible for disinfection or sterilising of the closures 2, notably with the reduced diameter of rotor 10 and the compact form of device 1 as a whole.

With the drive 17 the rotor 10 is driven in pulses about the machine axis MA such that the rotor 10 in each movement phase of the pulsed rotary movement executes a rotation step corresponding to the pitch spacing of two closure holders 11, and in each stoppage phase of the pulsed rotary movement an empty closure holder 11 stands below the closure supply 20, via which the closure holder 11 is then filled completely with closures from the closure transport section 21. With the pulsed rotary movement of the rotor 10, the closure holders 11 each filled with closures 2 are moved along the UV lamps of the treatment section formed by the UV lamps 17 and 18 and extending over the angular region between the closure supply 20 and the closure discharge 22 and thus are disinfected by the UV light or UV radiation from the activated UV lamps 17 and 18.

Figure 1:
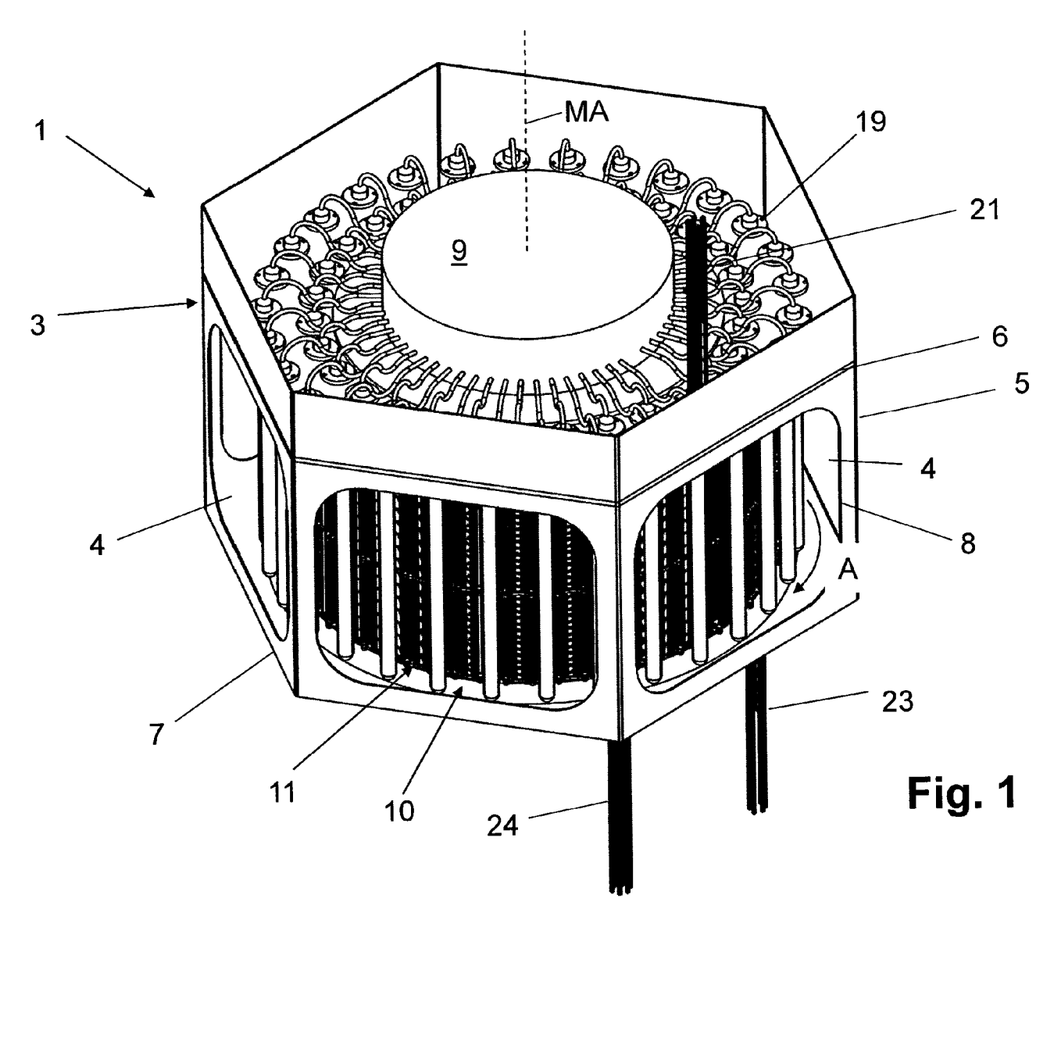
FIG. 1 in perspective view a device according to the invention for sterilising closures which are intended to close bottles or similar containers.
Figure 2:
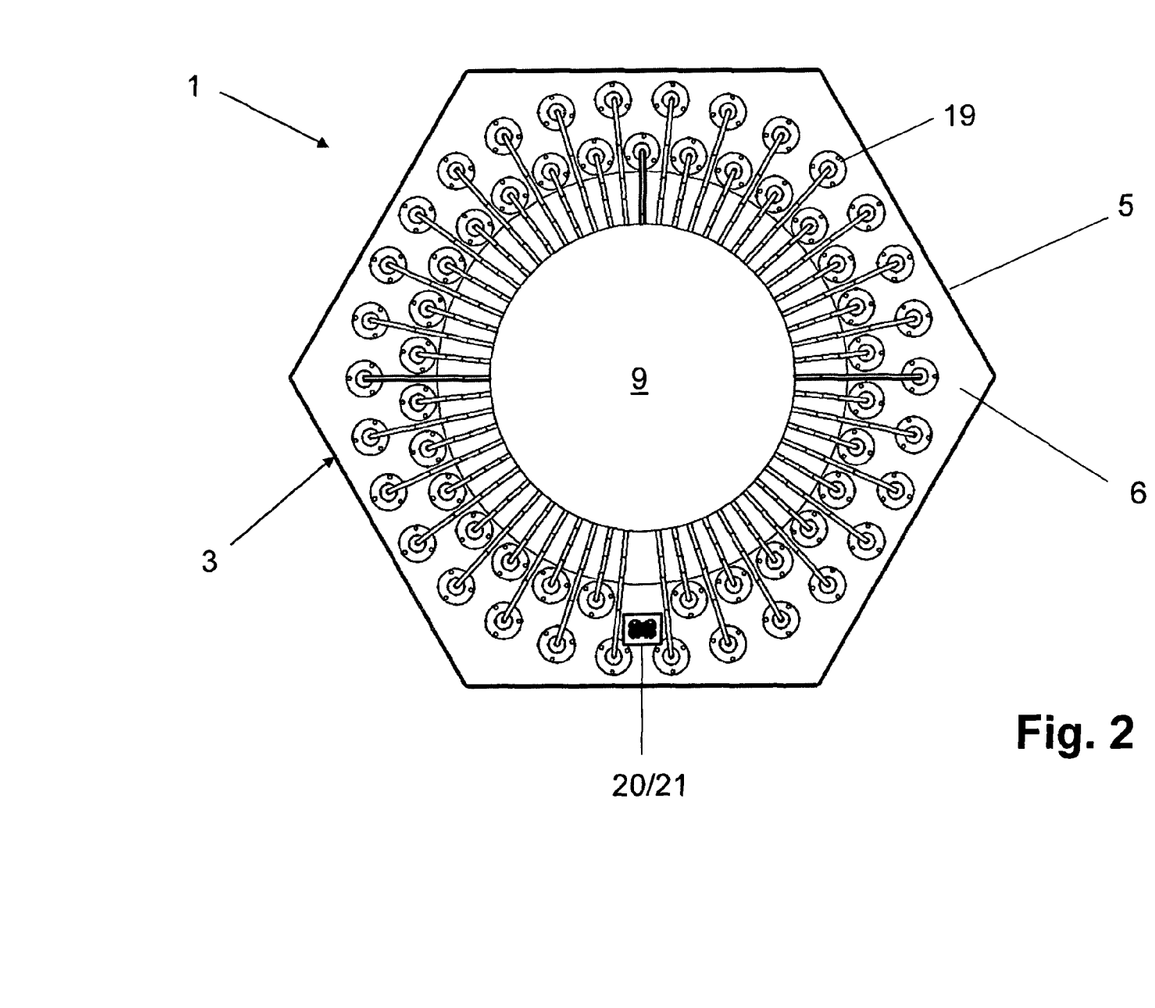
FIG. 2 a top view of the device in FIG. 1.
Figure 3:
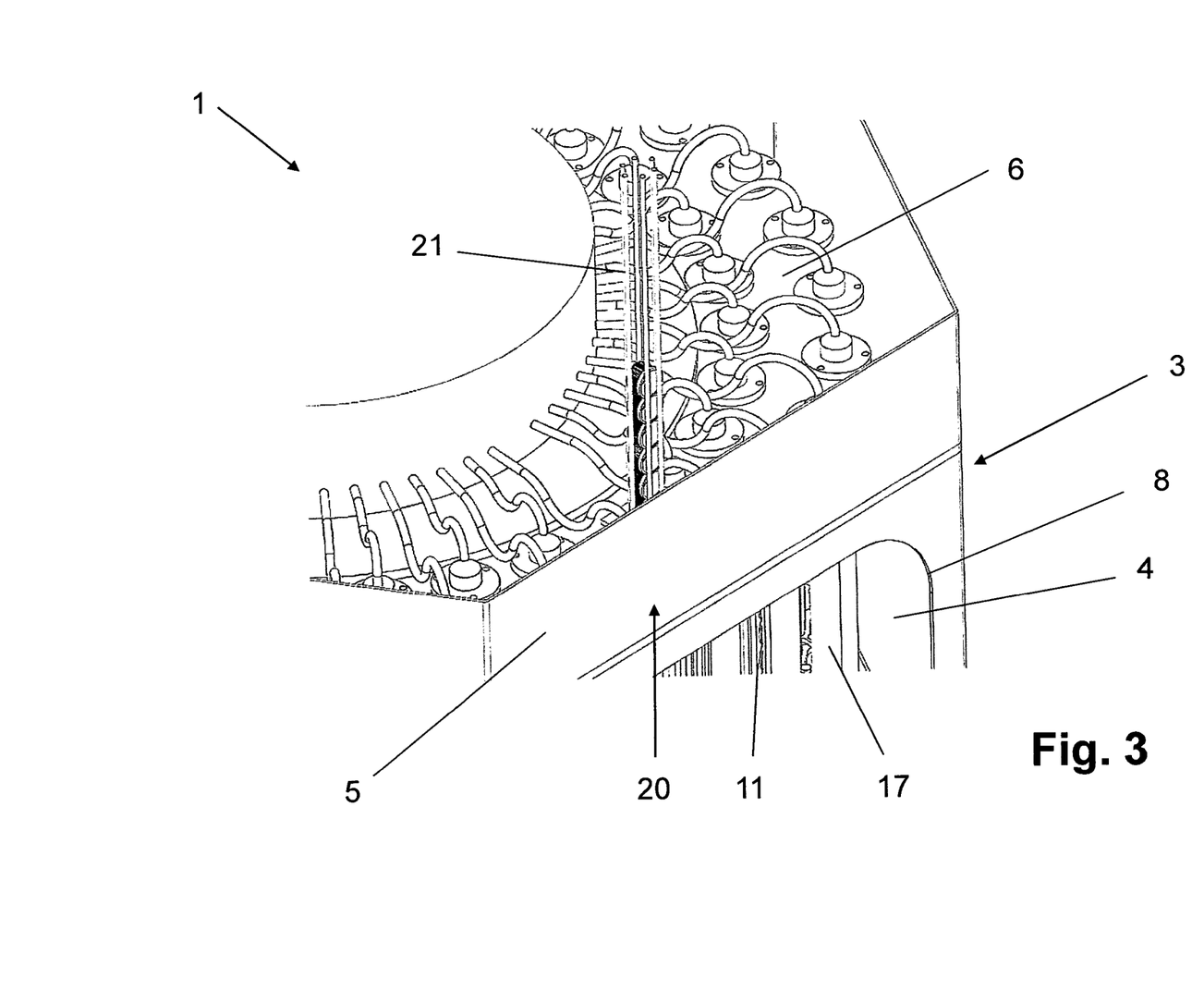
FIGS. 3 and 4 in perspective part view, the device in FIG. 1 in a view from above.
Figure 4:
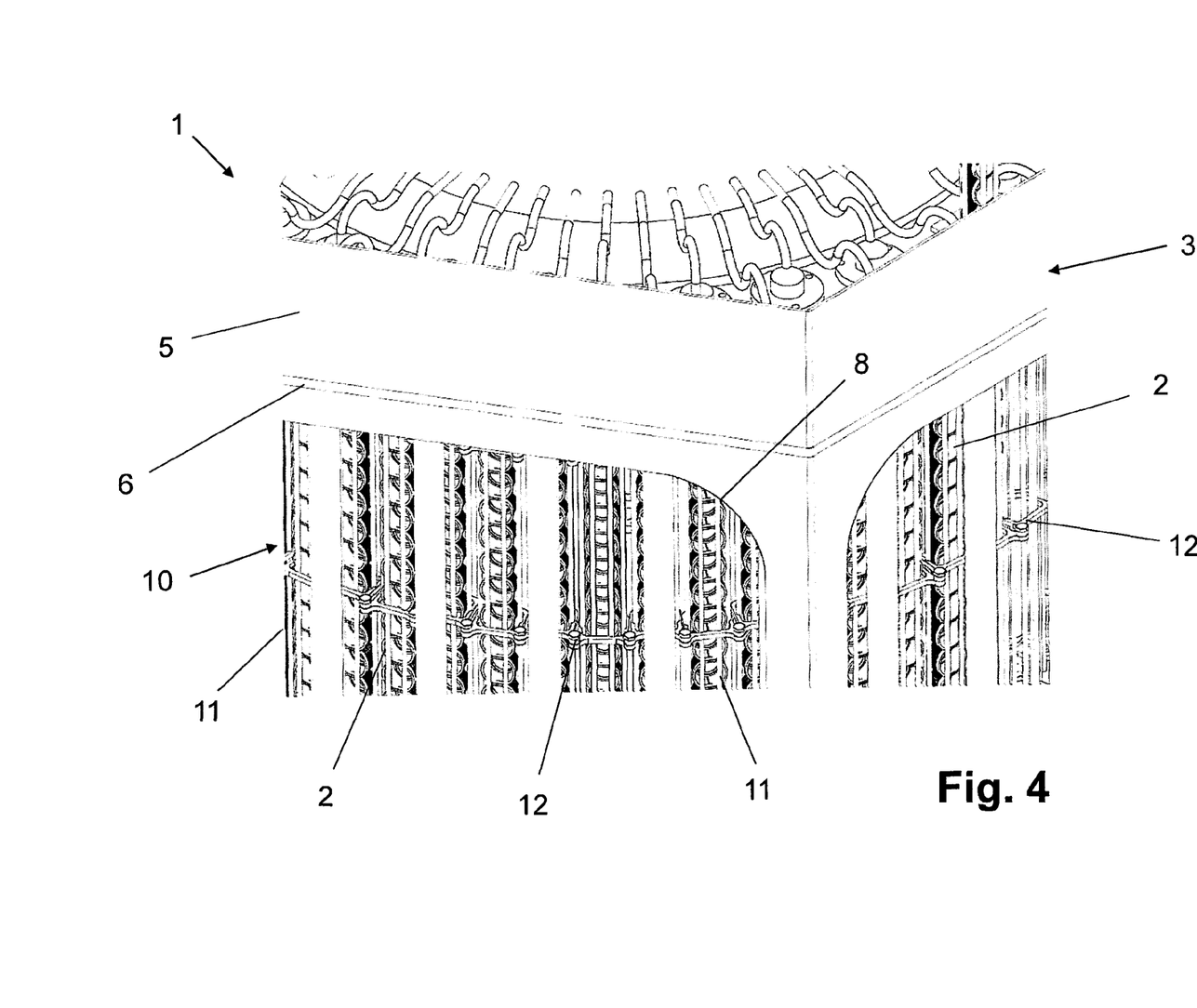
Figure 5:
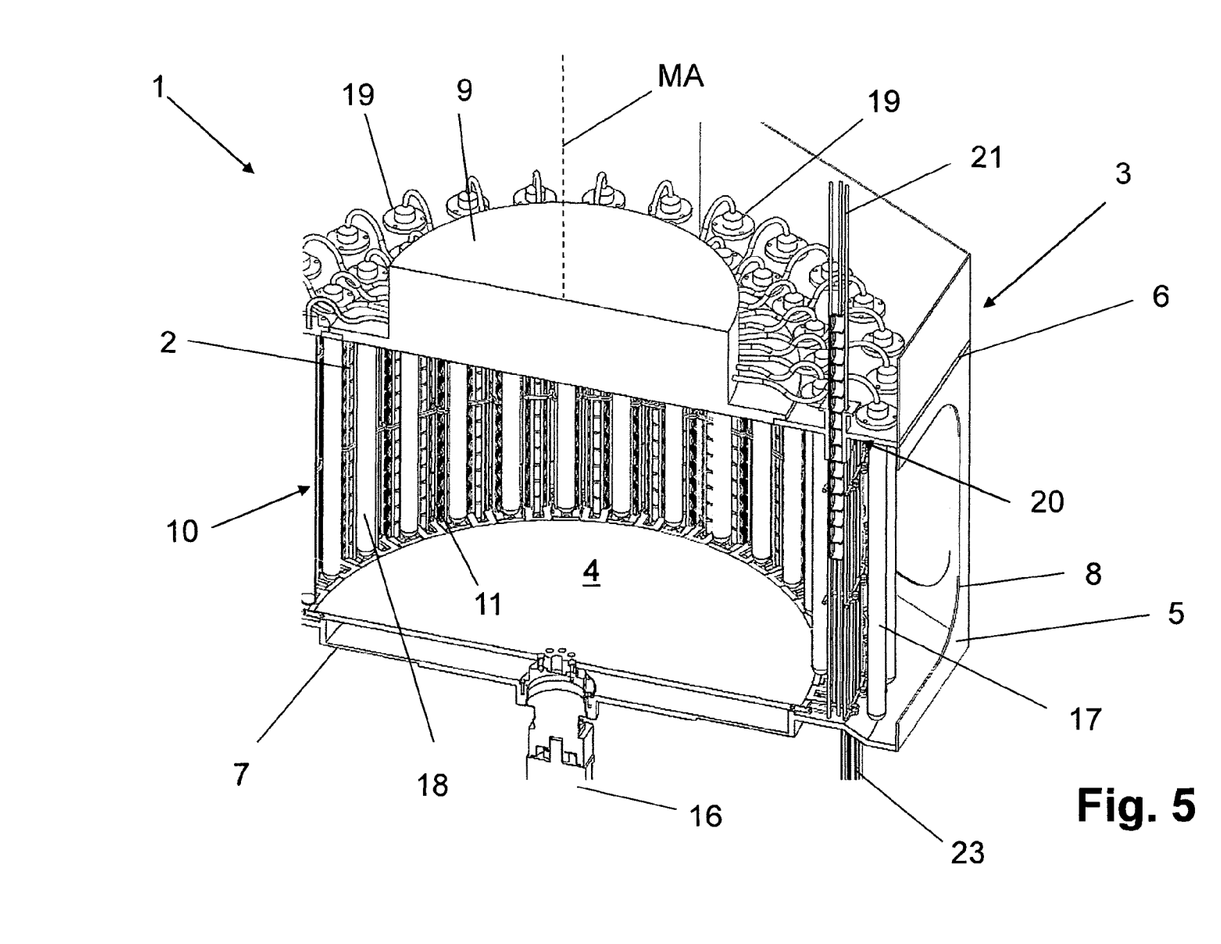
FIG. 5 the device in FIG. 1 in perspective view and in cross section.
Figure 6:
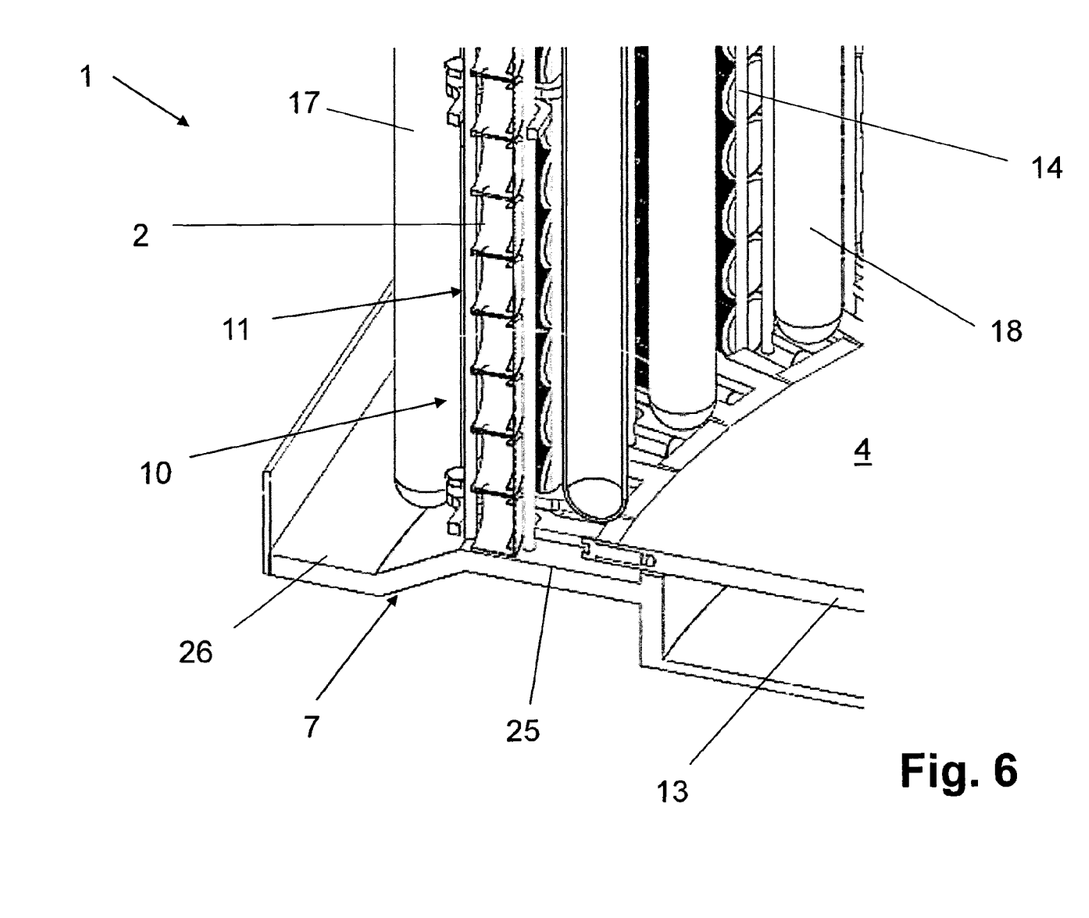
FIG. 6 an enlarged part depiction of FIG. 5.
Figure 7:
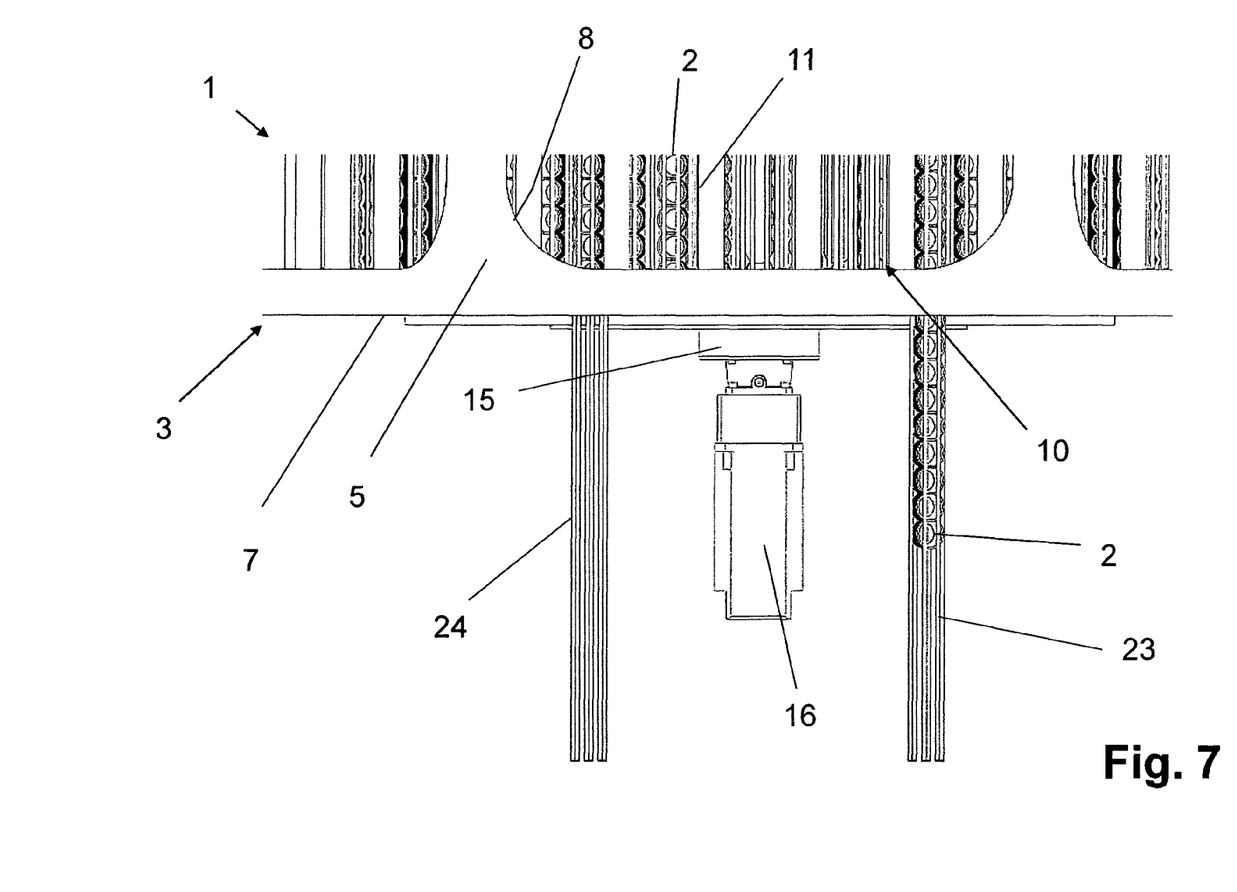
FIG. 7 the device in FIG. 1 in side view and in the region of a lower closure discharge or closure transport section.
Figure 8:
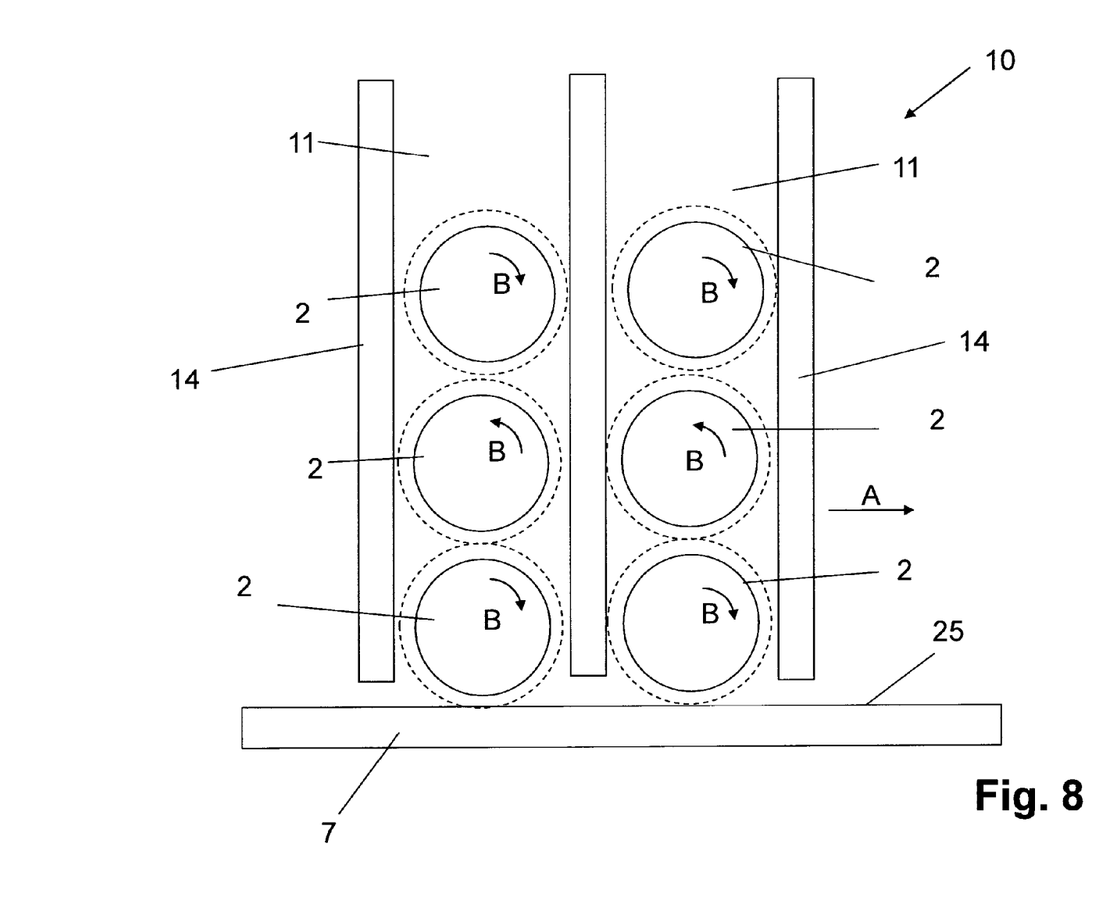
FIG. 8 in simplified part view and in side view, two closure holders formed on a rotor of the device.

As shown in FIG. 8, on UV treatment, because of the rotary motion of rotor 10 indicated by arrow A, the bottom closure arranged in respective closure holder 11 rolls with its peripheral surface in the manner of a friction wheel on the closure contact surface 25 formed by the lower housing wall 7 and not moving with the rotor 10, whereby according to arrows B for each of the lowest closures 2 a rotary or rolling motion is generated which is transferred from closure to closure, to all closures 2 arranged in the respective closure holders 11 and lying on each other with their peripheral surfaces, so that finally all closures 2 in each closure holder 11 rotate in opposing directions according to arrows B and are thus exposed to UV radiation over their entire surface and optimally disinfected or sterilised.

Every time a closure holder 11 of the rotor 10 reaches the closure supply 22, all sterilised closures 2 of this closure holder fall onto the closure transport section 23 via which the disinfected or sterilised closures are then supplied for further use.

UV lamps 17 and 18 are activated constantly for example during operation of the device 1. Taking into account the diameter of the rotor 10, the speed of the pulsed rotary movement of the rotor 10 is selected such that the duration which the closure holders 11 require for movement from the closure supply point 20 to the closure discharge 22 corresponds to the treatment time necessary for the desired sterilisation level, for example a treatment time of 120 seconds.

In principle however it is also possible to design the control of the UV lamps 17 and 18 such that these can be switched on and off in particular to control the UV radiation power, i.e. can be operated in cycles or pulses.

To prevent the penetration of germs into the interior 4 of the housing 3, this interior is exposed to a positive pressure, for example a positive pressure of sterile air. The disinfection or sterilisation of the closures 2 takes place firstly directly by the UV radiation (UV-C radiation) but also supported by the ozone generated by this UV radiation which collects in the interior 4.

The particular advantages of the device 1 are that chemical-free sterilisation or disinfection of the closures 2 takes place, that the device 1 can be produced compactly with low construction volume, that high disinfection rates are possible wherein the disinfection power in particular can be set also by the speed of the pulsed rotary movement of the rotor 10 and/or by the UV power emitted by the UV lamps 17 and 18, and that by the own rotation of closures 2 (arrow B) in the closure holders 11, a constant reproducible quality of sterilisation or disinfection is achieved. A further essential advantage lies in the reduced operating costs of the device 1 which are due in particular to the relatively low energy consumption for the UV lamps 17 and 18 and the relatively long service life of these lamps (up to 15,000 operating hours).

In addition to the function elements described above, the device 1 for example also has devices for cleaning, in particular for foam cleaning, of the device, devices for extraction of ozone, measurement and monitoring devices or equipment, in particular also for function monitoring of the UV lamps 17 and 18, and nozzles for transport of closures 2 by conveyor air etc.

The invention has been described above with reference to one embodiment example. It is evident that numerous modifications and derivations are possible without leaving the inventive concept fundamental to the invention.

It has been assumed above that the sterilisation or disinfection of closures 2 takes place in a single rotor 10 or the closure holders 11 fitted there. In principle however it is possible to structure to device in the mariner of a cascade or modular, namely for example with at least two rotors 10 which are then arranged with their rotor axes e.g. coaxial, namely such that the closures 2 treated in a first rotor 10 at the closure discharge from this rotor do not enter the closure transport section 23 but via a closure supply enter a closure holder 11 of the further rotor 10, with which the closures 2 are then moved through a further treatment zone or section, for example a further UV treatment zone. In principle in particular with such a cascade-like or modular structure, there is also the possibility of providing at least two treatment zones with different treatment media.

LIST OF REFERENCE NUMERALS

1 Device
2 Closure
3 Device housing
4 Interior
5 Peripheral wall
6 Upper housing wall
7 Lower housing wall
8 Dome-like segment of upper housing wall
9 Housing part
10 Rotor
11 Closure holder
12 Holder
13 Carrier element
14 Closure guide element
15 Bearing 16 Drive
17, 18 UV lamps
19 Lamp holder
20 Closure supply
21 Closure transport section
22 Closure discharge
23 Closure transport section
24 Closure guide
25 Surface
26 Recess
A Direction of rotation of rotor 10
B Direction of rotation of closures 2
MA Machine axis

The invention claimed is:

1. An apparatus for sterilizing cap-like closures for closing bottles, said apparatus comprising a conveying system to move said cap-like closures through a treatment zone in which said cap-like closures are exposed to ultraviolet radiation for sterilization, said treatment zone comprising a multiplicity of ultraviolet radiation sources for emitting ultraviolet light, wherein said conveying system, in said treatment zone, comprises a rotor that can be driven to rotate about a vertical rotor axis, and a multiplicity of closure holders formed on a periphery of said rotor, each closure holder being oriented with a longitudinal extension thereof in a direction of said rotor axis, said closure holders being configured for moving said cap-like closures vertically from top to bottom through said treatment zone on a treatment section between a closure supply and a closure discharge.

2. The apparatus of claim 1, wherein said rotor comprises one of a hollow drum and a cylinder, said one of a hollow drum and a cylinder comprising a cage-like drum casing formed by said multiplicity of closure holders, wherein each of said closure holders is a cage-like closure holder having closure guide rails extending along a longitudinal direction thereof, said cap-like closures being held between said closure guide rails, wherein said closure guide rails are selected from the group consisting of rod-like closure guide rails and bar-like closure guide rails.

3. The apparatus of claim 1, wherein said ultraviolet radiation sources each comprise a longitudinal extension extending in a direction of said rotor axis.

4. The apparatus of claim 3, wherein each of said ultraviolet radiation sources comprises several ultraviolet radiators offset relative to each other along said longitudinal extension.

5. The apparatus of claim 3, wherein each of said ultraviolet radiation sources comprises a rod-like ultraviolet lamp.

6. The apparatus of claim 1, wherein said ultraviolet radiation sources are provided inside a movement track of said closure holders, wherein said ultraviolet radiation sources do not rotate with said closure holders, and wherein said ultraviolet radiation sources do not rotate with said rotor.

7. The apparatus of claim 1, wherein said ultraviolet radiation sources are provided outside a movement track of said closure holders, wherein said ultraviolet radiation sources do not rotate with said closure holders, and wherein said ultraviolet radiation sources do not rotate with said rotor.

8. The apparatus of claim 1, wherein said ultraviolet radiation sources are arranged suspended on a housing wall closing a top of an interior of said apparatus.

9. The apparatus of claim 1, wherein said ultraviolet radiation sources comprise inner ultraviolet radiation sources on an inside of a movement track of said closure holders and outer ultraviolet radiation sources on an outside of said movement track, wherein said inner and outer ultraviolet radiation sources are arranged opposite and offset each other such that each inner ultraviolet radiation source in relation to said rotor axis lies opposite a gap between two outer ultraviolet radiation sources.

10. The apparatus of claim 1, wherein said treatment zone is subjected to a positive pressure of a sterile medium, said sterile medium being selected from the group consisting of a sterile gaseous medium, a sterile vaporous medium, and sterile air.

11. The apparatus of claim 1, wherein each closure holder comprises a lower open end provided opposite a closure contact surface that moves relative to said rotor and on which a closure adjacent to said closure contact surface rolls during circulation of said rotor, thereby generating a closure rotary movement transmitted from closure to closure in said closure holder.

12. The apparatus of claim 1, further comprising additional rotors succeeding each other in a transport direction of said cap-like closures, each of which is arranged in a treatment zone and each of which comprises a multiplicity of closure holders.

* * * * *